(12) United States Patent
Klobe

(10) Patent No.: US 7,229,422 B2
(45) Date of Patent: Jun. 12, 2007

(54) SUCTION CUP FOR NON-SURGICAL CORRECTION OF THE FORM AND/OR FUNCTIONALITY OF THE CHEST

(76) Inventor: Eckart Klobe, L 11,3, D-68161 Mannheim (DE)

( * ) Notice: Subject to any disclaimer, the term of this patent is extended or adjusted under 35 U.S.C. 154(b) by 387 days.

(21) Appl. No.: 10/502,918

(22) PCT Filed: Jan. 22, 2003

(86) PCT No.: PCT/DE03/00161

§ 371 (c)(1),
(2), (4) Date: Jul. 28, 2004

(87) PCT Pub. No.: WO03/063752

PCT Pub. Date: Aug. 7, 2003

(65) Prior Publication Data

US 2005/0119700 A1    Jun. 2, 2005

(30) Foreign Application Priority Data

Feb. 1, 2002  (DE) .............................. 102 04 078

(51) Int. Cl.
*A61H 7/00* (2006.01)
(52) U.S. Cl. ........................................................ 601/6
(58) Field of Classification Search .................. 601/6, 601/7, 9–11, 14, 41, 43; 604/74; 606/237
See application file for complete search history.

(56) References Cited

U.S. PATENT DOCUMENTS 2,078,536 A * 4/1937 Hardman ........................ 601/7
4,469,105 A * 9/1984 Staver ........................ 600/387
5,295,481 A * 3/1994 Geeham ....................... 601/43
6,098,205 A    8/2000 Schwartz et al.

FOREIGN PATENT DOCUMENTS

| DE | 2450098  | 10/1974 |
|----|----------|---------|
| DE | 19734571 | 8/1987  |
| DE | 4228406  | 8/1992  |
| DE | 9400822  | 1/1994  |
| EP | 0338524  | 4/1988  |

\* cited by examiner

*Primary Examiner*—Quang D. Thanh
(74) *Attorney, Agent, or Firm*—Galgano & Associates, PLLC

(57) ABSTRACT

The suction cup is placed in sealing contact on the anterior side of the torso. A partial vacuum can be applied to the body by the suction cup. The suction cup is composed at least in part of soft elastic materials. It is provided with inner flanks that flare toward the body when under atmospheric pressure. The suction cup bears with lateral body-fitting portions on each side of the sternum, with an upper body-fitting portion on the upper region of the sternum and with a lower body-fitting on the lower region or below the sternum. The deformability of the suction cup varies over its circumference. At least the upper, lower or one of the lateral body-fitting portions have different deformabilities.

19 Claims, 3 Drawing Sheets

SUCTION CUP FOR NON-SURGICAL CORRECTION OF THE FORM AND/OR FUNCTIONALITY OF THE CHEST

CROSS-REFERENCE TO RELATED APPLICATION

This application is a 371 of PCT/DEO3/00161 filed Jan. 22, 2003

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable

INCORPORATION-BY-REFERENCE OF MATERIAL SUBMITTED ON A COMPACT DISC

Not applicable

BACKGROUND OF THE INVENTION

1. Field of the Invention

The invention relates to a suction cup for nonsurgical correction of the form and/or functionality of the chest, which cup is placed in sealing contact on the anterior side of the torso and with which partial vacuum can be applied to the body.

Partial vacuum is to be understood as the value of a pressure difference relative to atmospheric pressure.

The purpose of the invention is to influence the anatomical configuration of the bones and cartilage of the chest, and especially to exert a bending moment on the bony and cartilaginous components of the ribs, sternum and costal arches, primarily for nonsurgical correction of funnel chest. The invention does not relate, or at best relates only secondarily, to cosmetic treatment of soft parts or reconstruction thereof.

2. Description of Related Art Including Information Disclosed Under 37 CFR 1.97 and 1.98

Among those skilled in the medical arts, surgery is the means of choice for effective correction of funnel chest (see Morphological and Biochemical Investigations in Funnel and Pigeon Chest Deformations with Consideration of the Non-Collagenous Cartilage Components, Sonja Nitsche, Faculty of Medicine of the Westphalian Wilhelm University at Munster, Dissertation 2000, pages 19 to 25). In that document, conservative measures—physiotherapy and orthopedic techniques—are described as incapable of correcting the funnel.

According to that source, purely cosmetic operations are available, but they merely conceal the visual appearance of the funnel. This is achieved, for example, by interposing suitable material under the skin or by detaching ribs from the sternum forming the funnel base, pulling them over the sternum to the opposite side, and fixing them on the opposite side. However, the effects of the funnel on the internal organs are not eliminated thereby. In other operations, the connection between the mesosternum and the xiphoid process is severed and then the underlying diaphragm is cut loose from the sternum, so that further inwardly directed tensile forces can no longer act on the sternum during inhalation. Such operations are temporary solutions, with which radical operations can be postponed. Radical operations range from those in which the sternum is removed to the combination of mobilization of the sternum and fixation in overcorrected position. In one of the common radical operations it is necessary to make a skin incision from the jugular fossa to the navel, to separate the musculature located on the thorax, to sever the origins of the abdominal muscle at the level of the xiphoid process, to make incisions into the costal perichondrium, to push the perichondrium carefully aside, to sever the cartilage, to break through the sternum and to fix it by means of a metal strap, which if necessary is supplemented by two further straps, the strap ends being bent by pliers in such a way that they fit the thoracic aperture and do not push up the overlying tissue, to fix the straps, if necessary to chamfer protruding rib processes, to attach a Redon drainage, to close the wound, to hospitalize the patient for 10 to 14 days, to provide intensive support measures by respiratory therapy and to leave the metal straps implanted in place for twelve months.

Elsewhere (see The Funnel Chest. Stages and Shape Correction, Dr. Hans Peter Hummer, Zuckschwerdt Verlag, Munich, Bern, Vienna, 1985, pages 10, 11, 26, 31 and 32), correction of funnel chest is divided into three phases— mobilization, stabilization and soft-tissue reconstruction— and it is pointed out, from the historical perspective, that success in funnel-chest operations was hampered at first by lack of stabilization options. That source describes among other possibilities the use of wires, nails, clasps or steel straps as auxiliary means, which are left in the body or which protrude out of the body for months or years, in order to give the thorax the necessary stability after completion of funnel-chest surgery (mobilization of the sternum). The same source indeed mentions alternatives for nonsurgical correction of funnel chest, but it describes them as ineffective, especially a correction by means of suction cups based on the publication of Spitzy, to be discussed below.

In Spitzy (Textbook of Pediatrics, Volume 8, Pediatric Orthopedics, Prof. Dr. Hans Spitzy, F. C. W. Vogel Verlag, Leipzig, $3^{rd}$ Edition, 1930, pages 196 and 197), it is described that, by using a glass bell over the depressed portion of a funnel chest and applying partial vacuum, an immediate alleviation of the funnel could be observed. However, the technique of the method was described as tricky, because it was difficult to fit the rigid wall of the suction cup used at that time to the uneven surfaces of the anterior thoracic wall.

From German Patent 19734571 A1 there is known, for treatment of funnel chest, a suction cup having a central, transparent plate and a rim that is matched or can be matched individually to the respective patient and that bears flexibly on his or her body. Reportedly, therapy units of 5 to 15 minutes can be administered one or two times per week with the suction cup.

Drawbacks of the prior art include the following: conservative methods are faced with a deep-rooted and widely held bias against options of this kind; cosmetic procedures achieve merely a purely cosmetic effect, which does not eliminate the effects of the funnel on the internal organs; separation of the diaphragm from the sternum represents a purely delaying tactic; radical operations impose a severe burden due to the operation and to the metal elements that remain implanted for months or years in order to fix the surgically treated funnel chest—quite aside from the patient's postoperative pain, which is sometimes considerable; for the suction cup according to Spitzy, no mention has been found of successful stabilization in the corrected condition; and the idea underlying German Patent 19734571 A1 has the disadvantage of short application units.

A cupping device having a suction cup is known from German Patent 4228406 C2.

BRIEF SUMMARY OF THE INVENTION

The object of the invention is to make a suction cup of the type described in the introduction sufficiently fit for everyday use that it satisfies the criteria below to the best possible extent:
1. The suction cup should be capable of ensuring not only mobilization of the sternum but also adequate stabilization of the sternum in corrected position. For this purpose it should be usable even outside therapeutic facilities, for large portions of the day and/or night, without greatly hampering the performance of body movements and/or activities that are common in general. This applies in particular to lying down, sitting, standing, walking, running, school attendance, office work, housework and various kinds of bodily effort or sports. For this purpose the suction cup must be convenient to wear and ensure good sealing.
2. It should be possible for the patient to operate the suction cup himself or herself with only occasional medical supervision. For this purpose, the suction cup should ensure a plurality of safety functions.
3. As regards its effect, the suction cup should have high functionality and be flexibly adapted to the individual anatomical needs of different users, without needing any kind of modifications. It should develop its main effect at the locations of maximum therapeutic efficacy. If the locations of maximum therapeutic efficacy change due to progress of the treatment, it should be capable of following these locations with its main effect.
4. By its more frequent use and in each case longer time of action of the suction cup, its therapeutic efficacy should be improved, and faster as well as more durable treatment success should be achieved. In particular, the time should be reached very quickly at which the funnel raised by the suction cup no longer collapses back into the old position during the intervals between individual applications, with positive consequences for the emotional state of the patient and his or her willingness to continue application.

The suction cup that achieves this object is composed at least in part of soft elastic material. It is provided with inner flanks that flare toward the body when under atmospheric pressure. The suction cup bears with lateral body-fitting portions on each side of the sternum, with an upper body-fitting portion on the upper region of the sternum and with a lower body-fitting portion on the lower region or below the sternum. The deformability of the suction cup varies over its central angle. At least the upper, lower or one of the lateral body-fitting portions have different deformabilities.

With increasing partial vacuum, the suction cup undergoes a deformation, by which its area of contact with the body becomes increasingly larger and by which the area overarched by it becomes increasingly smaller.

The following advantages are associated with the inventive suction cup:
1. The decrease of area overarched by the suction cup as the partial vacuum increases has two effects: the total suction forces and thus the total bearing forces vary subproportionally as the partial vacuum increases; and those areas which continue to be exposed to the increasing partial vacuum become progressively more limited. This benefits safety and wearing comfort while permitting locally different protection of body parts that are sensitive to suction force.
2. The inner flanks that flare toward the body and develop an increasingly larger area of contact with the body as the partial vacuum increases have two effects during increase of the suction forces: firstly a progressive decrease of those distances that part of the body can move toward the inner arch of the suction cup before it abuts thereon; and secondly they increasingly permit—inasmuch as they themselves are composed of soft elastic material—natural motor movements of the body without loss of suction adhesion of the suction cup. On the one hand this permits a safety function relative to body parts that are sensitive to stretching, and on the other hand it permits the performance of natural body movements without thereby interrupting the therapeutic effect of the suction cup.
3. By the inner flanks that flare toward the body, the regions of maximum exertion of bending moment can be applied where the bones and cartilage have been severed or cut into during common surgical corrections for mobilization of the funnel: in the region of the periphery of the funnel chest and in the region of the sternum. And, if the funnel shape changes—for example due to the progress of treatment—the region of maximum exertion of bending moment follows the respective periphery of the funnel chest and thus the region of therapeutically most effective exertion of bending moment.

Because the deformability of the suction cup varies over its central angle (i.e., circumference or periphery) the pressure per unit area that the suction cup develops when partial vacuum is applied also varies over its central angle (i.e., circumference or periphery)

The term deformability can encompass deformation resistance with respect to the creation of a deformation pathway, restoring force after creation of a deformation pathway, and deformation pathway while the action of a force is being experienced. The deformability can be tested by applying, perpendicular to the inner flanks of the suction cup, the end face of a cylindrical tester, whose cylinder radius can be 8 mm.

Because the deformability of the suction cup varies over the central angle, it is possible to endow preferred sectors with the aforesaid advantages. This concerns especially sectors with low exertion of pressure, for protection of regions sensitive to pressing force, sectors with low exertion of suction force, for protection of regions sensitive to suction force, sectors with narrower limitation of stretching, for protection of regions sensitive to stretching, sectors of increased tolerance to natural motor movements, in order to increase moving comfort, and sectors of greater or lower exertion of bending moment, in order to treat regions requiring greater or smaller effect as well as to predetermine preferred directions for the bending moments to be exerted.

In a preferred embodiment, the poorly or not readily deformable lateral body-fitting portions of the suction cup are disposed on both sides of the sternum, the moderately deformable upper body-fitting portion is disposed in the upper region of the sternum, and the readily deformable lower body-fitting portion is disposed in the lower region or under the sternum. Thus the pressure per unit area acting on the pressure-sensitive body region under the costal arches, which region is essentially supported by musculature, is smaller than on the less sensitive body region in the upper region of the sternum. The highest pressure per unit area acts on the rib bones (os costale) and on the cartilaginous bridges (cartilago costale) extending these to the sternum, so that the main bending axis runs vertically.

In a preferred embodiment, the material of the body-fitting portions is homogeneous and its variations in deformability are achieved by local thickness variations. It must be noted, however, that it would also be possible to achieve the variations in deformability of the body-fitting portions by variation of their material characteristics, or to combine variation of the material characteristics with thickness variation.

In a preferred embodiment, the lateral body-fitting portions of the suction cup are the thickest. The upper body-fitting portion is thinner and the lower body-fitting portion is thinnest.

In a preferred embodiment, the body-fitting portions of the suction cup are made of silicone. From the chemical viewpoint, the common generic term "silicone" used here means polyorganosiloxane. This material is characterized by very good elastic deformability and skin tolerance. The good skin tolerance results substantially from good permeability for oxygen, nitrogen, carbon dioxide and water vapor. The silicone can be processed by an uncomplicated, shape-imparting technique, especially casting or injection molding. The silicone is preferably addition-cross-linking, but can also be condensation-cross-linking or radical-cross-linking. Processing takes place preferably at room temperature, but if desired can be accelerated by raising the temperature or by photopolymerization.

In a preferred embodiment, the body-fitting portions of the suction cup have a hardness of between 1 Shore A and 35 Shore A.

In a preferred embodiment, the suction cup is composed of a substantially rigid middle part and an apron of soft elastic material, especially silicone (polyorganosiloxane), mounted thereon and imparting a sealing effect.

In a preferred embodiment, the middle part, viewed in its basic outline, has the form substantially of a circle, segment of a circle or sector of a circle.

In a preferred embodiment, the middle part of the suction cup, viewed in its basic outline, has lateral indentations whose rim contours are substantially arcs of circles. The indentations are provided as spaces for female breasts.

In a preferred embodiment, the apron becomes broader from the middle part outward. In this case the lateral body-fitting portions have the smallest span outward from the middle part, the upper body-fitting portion has a larger span and lower body-fitting portion has the largest span.

In a preferred embodiment, the apron, all around, tapers away from the middle part to a greater or lesser degree.

In a preferred embodiment, the cross section of the apron is substantially triangular or trapezoidal. However, the apron can also have concave or convex curvature.

In a preferred embodiment, the middle part is plane. The apron has a border disposed in a plane parallel to the plane of the middle part. However, the border can also have concave or convex curvature.

The middle part can also have convex curvature and, in fact, preferably slightly convex curvature.

In a preferred embodiment, the apron of the suction cup is produced by a shape-imparting method, especially casting or injection molding. The middle part is embedded in the apron.

In a preferred embodiment, at least the portion of the middle part not covered by the apron is transparent. Thereby the patient can directly follow the progress of the treatment visually, which is of considerable importance for his or her motivation.

In a preferred embodiment, the middle part is equipped with a port for application of partial vacuum.

In a preferred embodiment, the partial vacuum that can be applied to the suction cup is limited by design. This is tantamount to limitation by design of the maximum pressure per unit area that can be exerted with the suction cup. This is an important safety feature, especially when the use of the suction cup is left to a medical layperson. Limitation of the partial vacuum can be achieved in various ways by design. For example, the deformability of the suction cup can be configured in such a way that the cup collapses completely if the partial vacuum exceeds a predetermined limit value. Another possibility is to equip the suction cup with a pressure-operated safety valve. Finally, the partial vacuum can be limited simply by the type of suction pump connected to the suction cup.

In a preferred embodiment, the suction pump is a hand pump. It can be carried along with ease, and it does not depend on an external energy supply. This is of great importance for everyday usability of the suction cup.

In a preferred embodiment, the partial vacuum that can be built up in the suction cup by means of the hand pump is limited by design by virtue of the type of hand pump. This is a safety feature. Experience shows that a partial vacuum of about 0.4 bar is quite sufficient. This can be built up with a small, inexpensive hand pump, which has an actuating element in the form of an elastically compressible ball, which fits easily into a shirt or coat pocket. It must be noted that a higher partial vacuum and a correspondingly stronger force effect can also be achieved with a pump of different type, but the use thereof must be reserved to medical professionals.

BRIEF DESCRIPTION OF THE SEVERAL VIEWS OF THE DRAWINGS

The invention will be explained in more detail hereinafter by means of practical examples illustrated in the drawing, wherein.

DETAILED DESCRIPTION OF THE INVENTION

Figure 1:
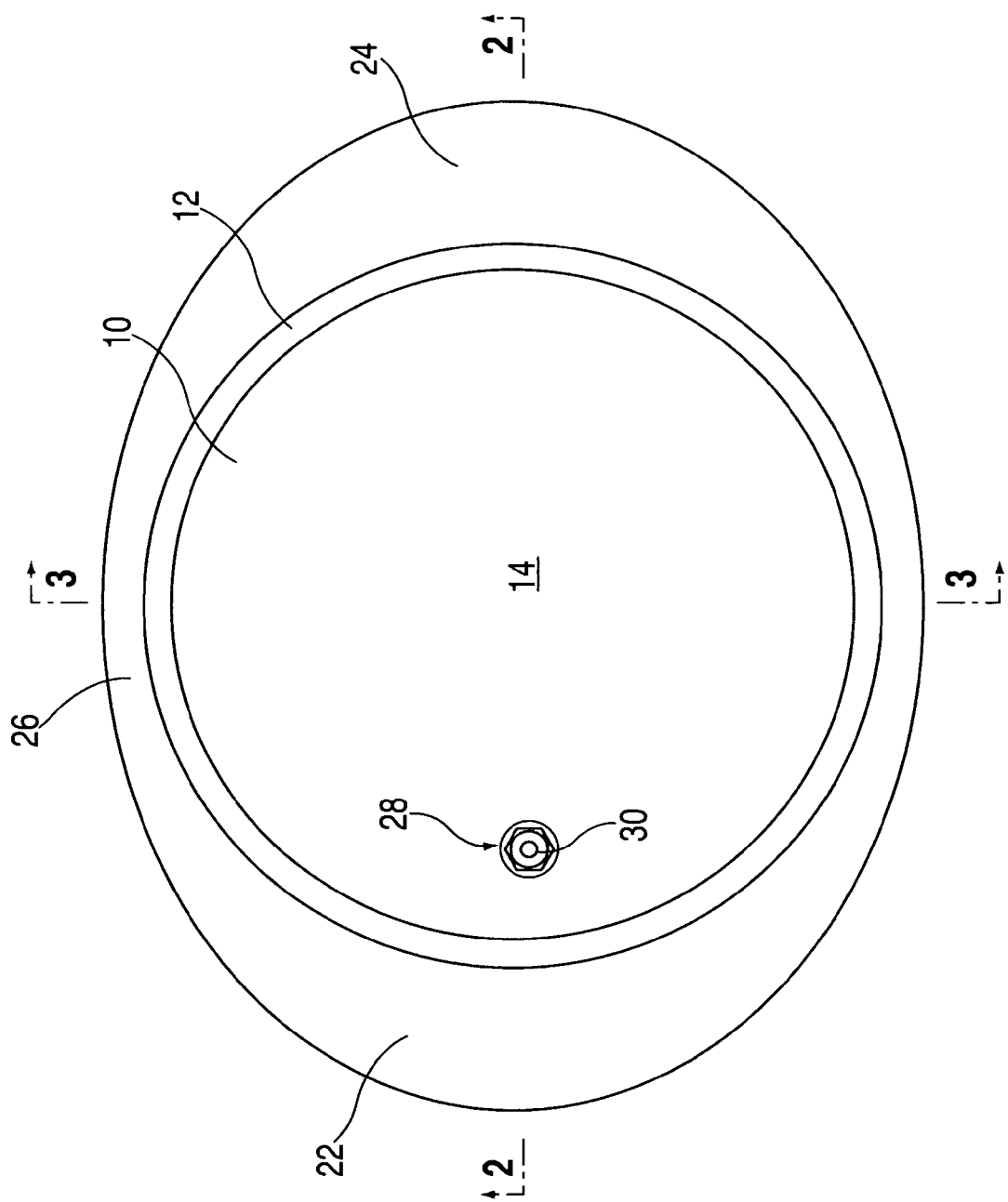
FIG. 1 shows a horizontal projection of a suction cup.
Figure 2:
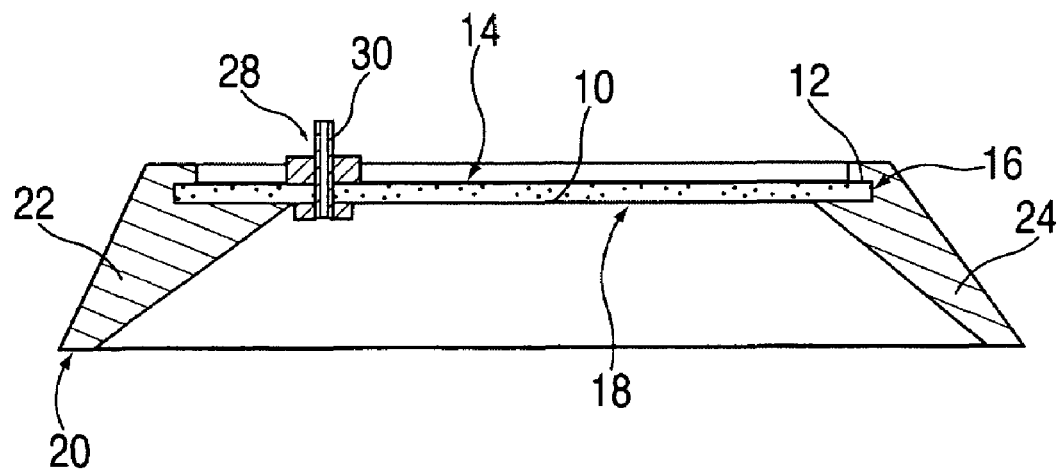
FIG. 2 shows a longitudinal section through the suction cup along line 2—2 in FIG. 1.
Figure 3:
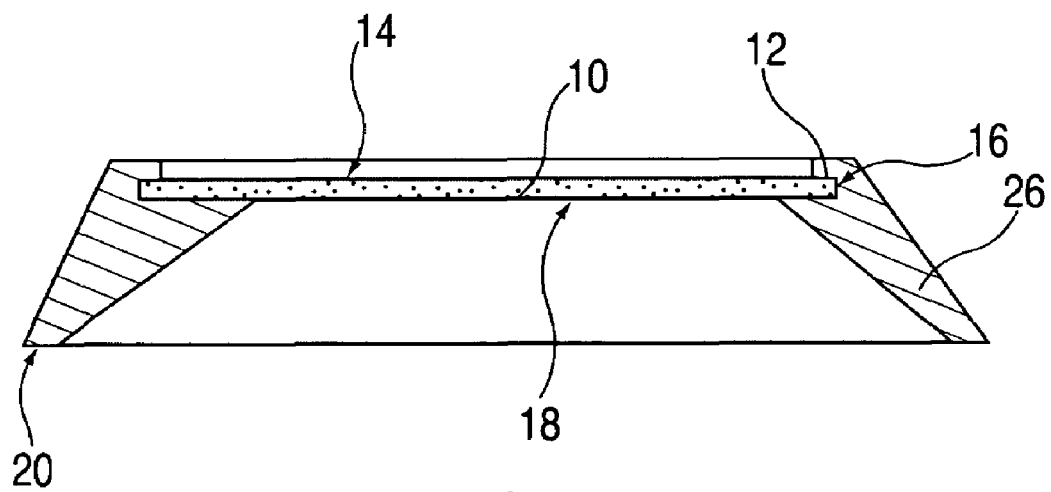
FIG. 3 shows a cross section through the suction cup along line 3—3 in FIG. 1.

The suction cup according to FIG. 1 to FIG. 3 has a middle part in the form of a circular plate 10, which is plane, relatively rigid and transparent. Plate 10 is made of shatterproof plastic.

Figure 4:
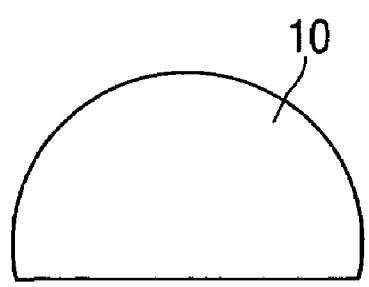
FIG. 4 to FIG. 7 show basic outlines of various middle parts of suction cups.
Figure 5:
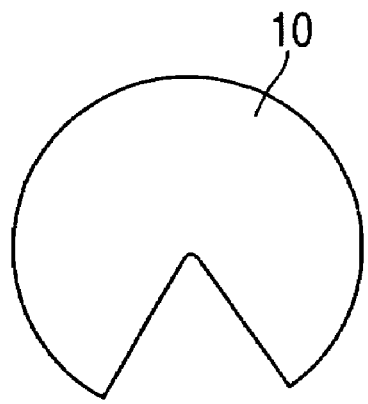
Figure 6:
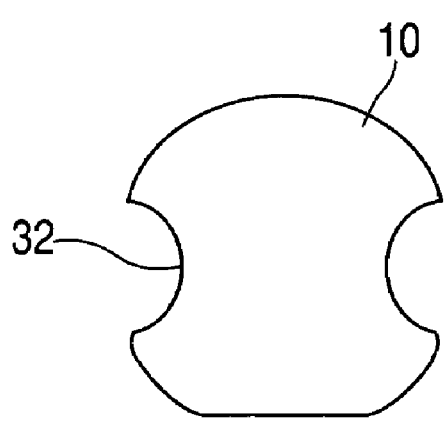
Figure 7:
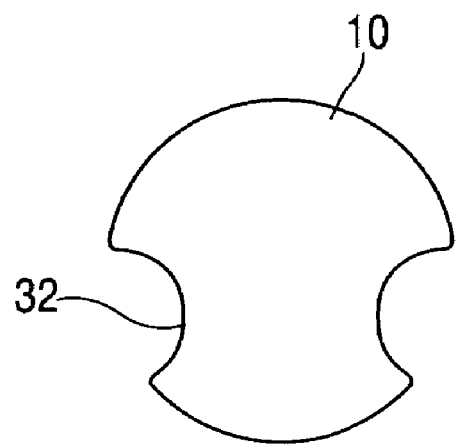

FIG. 4 to FIG. 7 show other possible basic outlines of plate 10. The basic outlines according to FIG. 4 and FIG. 6 are segments of circles. The basic outline according to FIG. 5 is a sector of a circle. The basic outlines according to FIG. 6 and FIG. 7 have lateral indentations 32 whose rims have the form of arcs of a circle.

Returning now to FIG. 1 to FIG. 3, plate 10 is set all round its periphery in an apron of soft elastic silicone (polyorganosiloxane). By means of a narrow and uniformly thick collar 12, the apron projects over the outer face 14 of plate 10, and it covers the side edge 16 thereof. The apron overlaps the inner face 18 of plate 10 for a width larger than that of collar 12. Plate 10 does not have to be transparent in the overlapped area, since the apron is nontransparent.

The apron extends outward from plate 10. It has a conical slope and a plane border 20, which is disposed in a plane parallel to plate 10.

The cross section of the apron is substantially trapezoidal. All around, the apron tapers toward border 20.

Where the apron bears on the patient in the upper sternum region, it has a moderate extent of span outward from plate 10. Body-fitting portion 22 of the apron has medium thickness here.

Where the apron bears on the patient's costal arches, opposite the upper sternum region, it has a greater span outward from plate 10. Body-fitting portion 24 is the thinnest here.

Where the apron bears on the patient's rib bones (os costale) and the cartilaginous bridges (cartilago costale) that extend them to the sternum on both sides, it has its smallest span outward from plate 10. The body-fitting portion 26 thereof is thickest here.

In the patient's upper sternum region, plate 10 is equipped with a port 28. This has a tube nozzle 30, over which there can be slipped a flexible tube leading to a hand pump. Port 28 can be made of plastic and be cemented into plate 10.

On the principle of operation: In the absence of external forces, and disregarding the weight of the suction cup, the suction force thereof is limited to that value of force that the rims of the suction cup are capable of applying as compressive force, preferably in the region of the periphery of the funnel chest. If the load-bearing capacity of the rims of the suction cup are limited by design in selected regions, the bearing pressure of the suction cup can be selectively limited in these regions. Correspondingly, exertion of bending moments by the suction cup can be influenced by design through the load-bearing capacity of its rims. Forces opposing such bending moments are the suction force in the region overarched by the suction cup and the retaining force of the ribs in the region of the spinal column.

The invention claimed is:

1. A suction cup for nonsurgical correction of the form and/or functionality of the chest in which the suction cup is placed in sealing contact on the anterior side of a torso of a patient and with which a partial vacuum can be applied to the torso, wherein the suction cup is composed of at least in part of soft elastic material, and is provided with inner flanks that flare toward the torso when under atmospheric pressure, the suction cup further comprising first and second lateral body-fitting portions each adapted to contact on opposite sides of a sternum of the patient, an upper body-fitting portion adapted to contact an upper region of the sternum and a lower body-fitting portion adapted to contact a lower region of, or below, the sternum, and wherein the suction cup has a circumference and a deformability that varies over its circumference and wherein the deformability of at least two members selected from the uroup consisting of said upper body-fitting portion, said first lateral body-fitting portion, said second lateral body-fitting portion and said lower body-fitting portion, is different.

2. A suction cup according to claim 1, wherein the lateral body-fitting portions are not-readily deformable, in that the upper body-fitting portion is moderately deformable, and in that the lower body-fitting portion is readily deformable.

3. A suction cup according to claim 1, wherein the material of the body-fitting portions is homogeneous and its variations in deformability are achieved by local thickness variations.

4. A suction cup according to claim 1, wherein the lateral body-fitting portions are thick, the upper body-fitting portion is thinner and the lower body-fitting portion is thinnest.

5. A suction cup according to claim 1, wherein the body-fitting portions are made of polyorganosiloxane.

6. A suction cup according to claim 1, wherein the body-fitting portions have a Shore hardness A of between 1 and 35.

7. A suction cup according to claim 1, wherein the partial vacuum that can be applied thereto is limited by a type of suction pump connected to the suction cup.

8. A suction cup according to claim 1, wherein the suction cup is connected to a suction pump comprising a hand pump which has an actuating element in the form of an elastically compressible ball.

9. A suction cup according to claim 1, wherein the suction cup is composed of a substantially rigid middle part and an apron of soft elastic material comprising polyorganosiloxane, mounted thereon and imparting a sealing effect.

10. A suction cup according to claim 9, wherein the middle part, has the form substantially of a circle, segment of a circle or sector of a circle.

11. A suction cup according to claim 9, wherein the middle part, has lateral indentations whose rim contours are substantially arcs of circles.

12. A suction cup according to claim 9, wherein the apron becomes broader from the middle part outward, and the lateral body-fitting portions have a smallest span outward from the middle part, the upper body-fitting portion has a larger span and lower body-fitting portion has a largest span.

13. A suction cup according to claim 9, wherein the apron, all around, tapers away from the middle part to a border.

14. A suction cup according to claim 9, wherein the cross section of the apron is substantially triangular or trapezoidal.

15. A suction cup according to claim 9, wherein the middle part has a plane, and the apron has a border disposed in a plane parallel to the plane of the middle part.

16. A suction cup according to claim 9, wherein the middle part has convex curvature.

17. A suction cup according to claim 9, wherein the apron is produced by a shape-imparting method and wherein the middle part is embedded in the apron.

18. A suction cup according to claim 17, wherein at least a portion of the middle part not covered by the apron is transparent.

19. A suction cup according to claim 9, wherein the middle part is equipped with a port for application of the partial vacuum.

* * * * *

UNITED STATES PATENT AND TRADEMARK OFFICE
CERTIFICATE OF CORRECTION

| | | |
|---|---|---|
| PATENT NO. | : 7,229,422 B2 | |
| APPLICATION NO. | : 10/502918 | |
| DATED | : June 12, 2007 | |
| INVENTOR(S) | : Eckart Klobe | |

It is certified that error appears in the above-identified patent and that said Letters Patent is hereby corrected as shown below:

Column 1, line 8, the reference to the PCT application "PCT/DEO3/00161" should read:

--PCT/DE03/00161--.

Column 3, lines 46-55, should read:

-- The suction cup that achieves this object is composed at least in part of soft elastic material. It is provided with inner flanks that flare toward the body when under atmospheric pressure. The suction cup bears with lateral body-fitting portions on each side of the sternum, with an upper body-fitting portion on the upper region of the sternum and with a lower body-fitting portion on the lower region or below the sternum. The deformability of the suction cup varies over its central angle, i.e., in circumferential direction. At least the upper, lower or one of the lateral body-fitting portions have different deformabilities. --

Column 4, lines 29-33, should read:

-- Because the deformability of the suction cup varies over its central angle the pressure per unit area that the suction cup develops when partial vacuum is applied also varies over its central angle. --

Column 7, line 40, cancel the text beginning with "1. A suction cup" to and ending with "portion is different." in Column 7, line 58 and insert the following claim:

--1. A suction cup for nonsurgical correction of the form and/or functionality of the chest in which the suction cup is placed in sealing contact on the anterior side of a torso of a patient and with which a partial vacuum can be applied to the torso, wherein the suction cup is composed at least in part of soft elastic material, and is provided with inner flanks that flare toward the torso when under atmospheric pressure, the suction cup further comprising first and second lateral body-fitting portions each adapted to contact on opposite sides of a sternum of the patient, an upper body-fitting portion adapted to contact an upper region of the sternum and a lower body-fitting portion adapted to contact a lower region of, or below, the sternum,

UNITED STATES PATENT AND TRADEMARK OFFICE
CERTIFICATE OF CORRECTION

PATENT NO.         : 7,229,422 B2
APPLICATION NO. : 10/502918
DATED               : June 12, 2007
INVENTOR(S)       : Eckart Klobe It is certified that error appears in the above-identified patent and that said Letters Patent is hereby corrected as shown below:

Column 7, line 40 (cont'd), and wherein the suction cup has a circumference and a deformability that varies in circumferential direction and is different between at least two members selected from the group consisting of said upper body-fitting portion, said first lateral body-fitting portion, said second lateral body-fitting portion and said lower body-fitting portion. --

Signed and Sealed this

Sixth Day of November, 2007

JON W. DUDAS
*Director of the United States Patent and Trademark Office*